United States Patent [19]

Neumann et al.

[11] Patent Number: 4,465,857
[45] Date of Patent: Aug. 14, 1984

[54] PHENYLHYDRAZONES

[75] Inventors: Peter Neumann, Wiesloch; Karl-Heinz Etzbach; Heinz Eilingsfeld, both of Frankenthal; Gerhard Hoffmann, Otterstadt, all of Fed. Rep. of Germany

[73] Assignee: BASF Aktiengesellschaft, Ludwigshafen, Fed. Rep. of Germany

[21] Appl. No.: 454,281

[22] Filed: Dec. 29, 1982

[30] Foreign Application Priority Data

Jan. 16, 1982 [DE] Fed. Rep. of Germany ....... 3201202

[51] Int. Cl.$^3$ ............................................. C07C 109/16
[52] U.S. Cl. ..................................... 564/251; 430/59; 430/73
[58] Field of Search ........................................ 564/251

[56] References Cited

U.S. PATENT DOCUMENTS 4,150,987 4/1979 Anderson et al.

FOREIGN PATENT DOCUMENTS 3124396 7/1982 Fed. Rep. of Germany .

Primary Examiner—Natalie Trousof
Assistant Examiner—L. Hendriksen
Attorney, Agent, or Firm—Oblon, Fisher, Spivak, McClelland & Maier

[57] ABSTRACT

Phenylhydrazones of the formula

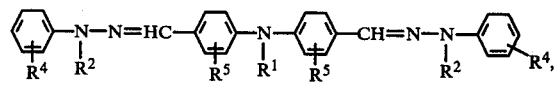

where $R^1$ is $C_1$–$C_4$-alkyl or phenyl-$C_1$–$C_4$-alkyl, or is phenyl which is unsubstituted or substituted by alkyl, alkoxy or halogen, or is a radical

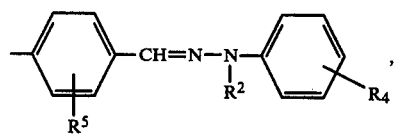

$R^2$ is alkyl or is phenyl which is unsubstituted or substituted by alkyl, alkoxy or halogen, and $R^4$ and $R^5$ independently of one another are each H, alkyl, alkoxy or halogen, are very useful as charge carrier-transporting compounds for electrophotographic recording materials.

13 Claims, No Drawings

PHENYLHYDRAZONES

The present invention relates to novel phenylhydrazones.

The novel phenylhydrazones are of the formula

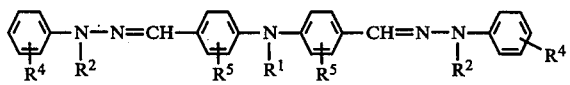
(I)

where $R^1$ is $C_1$–$C_4$-alkyl or phenyl-$C_1$–$C_4$-alkyl, or is phenyl which is unsubstituted or substituted by $C_1$–$C_4$-alkyl, $C_1$–$C_4$-alkoxy or halogen, or is a radical of the formula

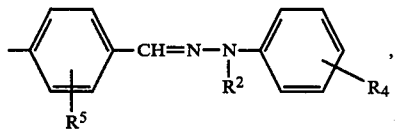

$R^2$ is $C_1$–$C_4$-alkyl or is phenyl which is unsubstituted or substituted by $C_1$–$C_4$-alkyl, $C_1$–$C_4$-alkoxy or halogen, and $R^4$ and $R^5$ independently of one another are each hydrogen, $C_1$–$C_4$-alkyl, $C_1$–$C_4$-alkoxy or halogen.

The phenylhydrazones I are very useful as charge carrier-transporting compounds for the production of electrophotographic recording materials.

The electrophotographic recording materials produced using the phenylhydrazones of the present invention exhibit substantially less discharge in the dark, rapid and complete discharge when exposed to actinic light and substantially greater differentiation between unexposed and exposed areas, with the result that substantially better toning of the exposed recording materials is obtained. In this respect, the phenylhydrazones of the present invention are substantially superior to 4-diethylaminobenzaldehyde-N',N'-diphenylhydrazone, which is disclosed in European Patent No. B-1,599 and is to be regarded as the most similar prior art compound to the compounds I.

Specific examples of $C_1$–$C_4$-alkyl radicals $R^1$ are methyl, ethyl, n- and i-propyl, n- and i-butyl and but-2-yl, of phenyl-$C_1$–$C_4$-alkyl radicals $R^1$ benzyl, 1- and 2-phenylethyl, 2- and 3-phenylpropyl and 2-, 3- and 4-phenylbutyl, and of unsubstituted or substituted phenyl radicals $R^1$ phenyl, 2-, 3- and 4-methylphenyl, 3- and 4-ethylphenyl, 3- and 4-isopropylphenyl, 4-butylphenyl, 2-, 3- and 4-methoxyphenyl, 4-ethoxyphenyl, 4-propoxyphenyl, 4-butoxyphenyl, 2-, 3- and 4-chlorophenyl, 2-, 3- and 4-bromophenyl, 4-iodophenyl and 4-fluorophenyl.

Halogen is preferably bromine and in particular chlorine. $R^1$ is preferably methyl, ethyl or phenyl.

Suitable radicals $R^2$ are the alkyl and phenyl radicals stated above for $R^1$. $R^2$ is preferably methyl, ethyl or phenyl.

Suitable $C_1$–$C_4$-alkyl radicals $R^4$ and $R^5$ are those stated for $R^1$. Specific examples of $C_1$–$C_4$-alkoxy are methoxy, ethoxy, n- and i-propoxy and n- and i-butoxy. Suitable halogens are bromine, fluorine and iodine, preferably chlorine, and $R^4$ is preferably in the 3- or 4-position. $R^4$ and $R^5$ are each preferably hydrogen.

Phenylhydrazones of the formula I where $R^1$ and $R^2$ are each methyl, ethyl or phenyl and $R^4$ and $R^5$ are each hydrogen are preferred because of their particularly advantageous properties.

Hydrazones of the formula Ia

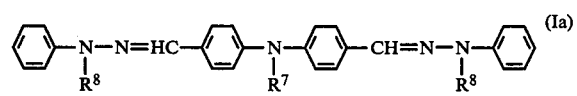
(Ia)

where $R^7$ and $R^8$ are each methyl or phenyl are particularly preferred.

Phenylhydrazones of the formulae

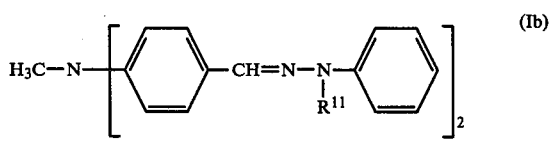
(Ib)

$R^{11} = $ —$CH_3$ or 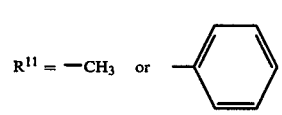

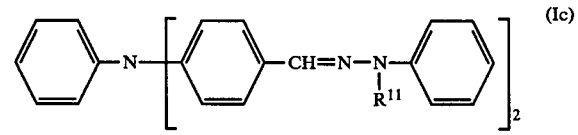
(Ic)

should be particularly singled out.

The phenylhydrazones I can be obtained by a conventional process, by reacting an appropriate 4-aminobenzaldehyde with an appropriate phenylhydrazine.

The reaction is preferably carried out in an organic solvent, in the presence or absence of an acid or base, at from room temperature (20° C.) to 200° C., preferably from 50° to 100° C.

Where the product is soluble in the solvent used, it may be precipitated by adding a non-soluble liquid, eg. water, and may be isolated by filtration.

If desired, the hydrazone may be still further purified by recrystallization or another conventional purification method.

The phenylhydrazines and aminobenzaldehydes required as starting materials are known or may be prepared by a conventional process.

The novel phenylhydrazones I can be used in single-layer and multi-layer electrophotographic recording materials. In the first of these, a layer containing the phenylhydrazone I as the charge carrier-transporting substance, together with a dye which produces charge carriers when exposed to actinic light, and a binder, is applied onto a conductive base.

In multi-layer systems, a first layer in which charge carriers are produced by exposure to actinic light is located on a conductive base, and a charge transport layer containing I is located on top of this first layer.

The production of such recording materials, and the materials, such as bases, binders and charge carrier-producing dyes, required for this purpose, are known.

Depending on the field of use of the recording materials, suitable bases are, for example, aluminum sheet, aluminum foil, polyester films coated by vapor deposition with aluminum, or pretreated aluminum bases such as those used in offset printing plates.

The choice of binder is governed by the field of use. Thus, for example, a polyester resin, PVC, polystyrene or a polycarbonate is used for the copying sector, while alkali-soluble binders are particularly suitable for planographic printing. For the purposes of the invention, alkali-soluble binders are those which are soluble in aqueous or alcoholic alkaline solvent systems. These binders are high molecular weight substances possessing alkali-soluble acidic groups, such as anhydride, carboxyl, phenolic hydroxyl, sulfonic acid, sulfonamide or sulfonimide groups. A binder having a high acid number is preferred since it is particularly readily soluble in aqueous/alcoholic alkaline solvent systems. Particularly suitable examples are copolymers of styrene with maleic anhydride, of styrene, acrylic or methacrylic acid with acrylates or methacrylates, and of acrylic or methacrylic acid with acrylates or methacrylates.

Copolymers of styrene and acrylic acid with or without maleic anhydride are very particularly suitable since their acid numbers can be particularly readily adapted to the particular requirements when they are used as binders. Amongst these copolymers, those containing from 55 to 77% by weight of styrene, from 5 to 25% by weight of acrylic acid and from 0 to 20% by weight of maleic anhydride have proved particularly advantageous.

Examples of suitable charge carrier-producing substances for single-layer systems are dyes from the triarylmethane, xanthene and/or cyanine series. Where the novel hydrazones I are employed, particularly good results are achieved using malachite green (C.I. Basic Green 4, C.I. No. 42,000), C.I. Basic Violet 1 (C.I. No. 42,535), Crystal Violet, C.I. Basic Violet 10 (C.I. No. 45,170) or C.I. Basic Red 1 (C.I. No. 45,160).

In multi-layer systems, the dye or the pigment is present in a separate charge carrier-producing layer. In this case, azo dyes, phthalocyanines, isoindoline dyes and perylenetetracarboxylic acid derivatives are known to be particularly effective. Excellent results are achieved with perylene-3,4,9,10-tetracarboxylic acid diimide derivatives mentioned in German Laid-Open Applications DOS No. 3,110,954 and DOS No. 3,110,960.

The Examples which follow illustrate the invention. Parts and percentages are by weight.

EXAMPLE 1

A mixture of 4.7 g of N-methyldiphenylamino-4,4'-dicarbaldehyde, 5.0 g of N-methyl-N-phenylhydrazine and 40 g of NMP (N-methylpyrrolidone) was stirred for 2 hours at 60° C., after which 40 g of ethanol were added dropwise and the mixture was left to cool to room temperature, while stirring. The precipitate was filtered off under suction, washed with ethanol and water, and dried. After recrystallization from ethylene glycol monoethyl ether, 4.5 g of the hydrazone of the formula

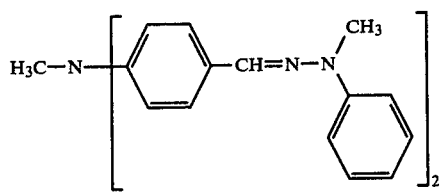

were obtained.

Mp. 200°–202° C.

| Analysis: | $C_{29}H_{29}N_5$ (M 448) | C | H | N |
|---|---|---|---|---|
| | calculated: | 77.82 | 6.53 | 15.65% |
| | found: | 77.6 | 6.4 | 15.7% |

EXAMPLE 2

A mixture of 4.7 g of N-methyldiphenylamine-4,4'-dicarbaldehyde, 8.82 g of N,N-diphenylhydrazine hydrochloride and 40 g of NMP were stirred for 2 hours at 60° C. The mixture was cooled to room temperature and then discharged onto 100 g of ice, and the precipitate was filtered off under suction, washed thoroughly with water and dried on clay. After recrystallization from ethanol, 2 g of the hydrazone of the formula

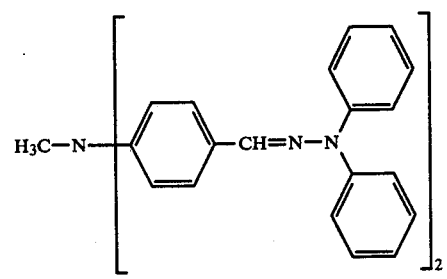

were obtained.

Mp. 158°–159° C.

| Analysis: | $C_{39}H_{33}N_5$ (M 572): | C | H | N |
|---|---|---|---|---|
| | calculated: | 81.93 | 5.82 | 12.25% |
| | found: | 81.7 | 5.8 | 12.1% |

EXAMPLE 3

6.0 g of a mixture essentially consisting of triphenylamine-4,4'-dicarbaldehyde and triphenylamine-4,4',4''-tricarbaldehyde and obtained by Vilsmeier formylation of triphenylamine were stirred with 5.0 g of N-methyl-N-phenylhydrazine in 30 g of NMP for 2 hours at from 50° to 60° C., after which the mixture was discharged onto 200 g of ice. The precipitate was filtered off under suction, washed thoroughly with water and dried on clay. The dry crude product was suspended in n-propanol and the suspension was heated at the boil for a short time. The precipitate obtained after cooling was filtered off under suction and dried. 5.1 g of a hydrazone mixture were obtained which contained, as the principal component, the hydrazone of the formula

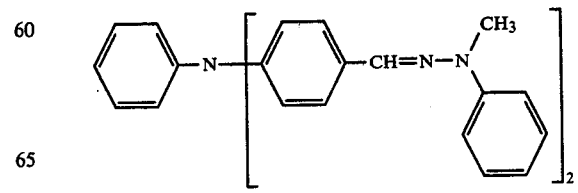

Mp. 160°–162° C.

EXAMPLE 4

6.0 g of a crude mixture essentially consisting of triphenylamine-4,4'-dicarbaldehyde and triphenylamine-4,4',4''-tricarbaldehyde and obtained by Vilsmeier formylation of triphenylamine were heated with 8.82 g of N,N-diphenylhydrazine hydrochloride in 30 g of NMP for 2 hours at 50°–60° C., after which the mixture was discharged onto 200 g of 50% strength ethanol. The precipitate was filtered off under suction, washed thoroughly with water and dried on clay. The dry crude product was recrystallized from n-propanol, a few drops of ammonia solution being added to the filtrate. 1.1 g of a hydrazone mixture were obtained which contains, as the principal component, the hydrazone of the formula

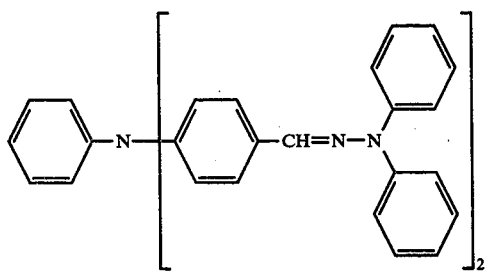

Mp. 127°–129° C.

USE EXAMPLE

Single-layer recording material 60 parts of a 76:24 styrene/methacrylic acid copolymer having a K value of 39.8 (measured on a 2% strength solution in dimethylformamide), 40 parts, in each case, of one of the phenylhydrazones I.1 to I.4 listed in Table Ia, and 0.6 part of C.I. Basic Violet 10 (C.I. No. 45,170) were dissolved in tetrahydrofuran. Using a reverse coating apparatus, the homogeneous solution was applied onto a finely brushed aluminum surface so as to give a layer which was 3.5+0.2 μm thick when dry.

TABLE Ia

Phenylhydrazones used

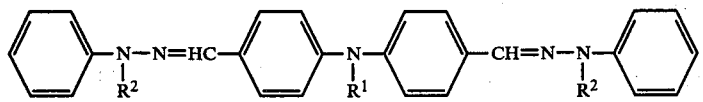

| Use Example | R¹ | R² | prepared according to Example |
|---|---|---|---|
| I.1 | —C₆H₅ | —C₆H₅ | 4 |
| I.2 | —C₆H₅ | —CH₃ | 3 |
| I.3 | —CH₃ | —C₆H₅ | 2 |
| I.4 | —CH₃ | —CH₃ | 1 |
| Comparative Compound | $(H_5C_2)_2N$—C₆H₄—CH=N—N(C₆H₅)₂ | | Europeon Patent 1599 |

The layers were then charged uniformly with a −8.5 kv d.c. corona at a distance of 1 cm, and then exposed to white light with an intensity of about 0.85 mw.cm$^{-2}$. The following measurements were made on the plates treated in this manner:

Parameter A: surface potential, in volts, achieved after a charging time of 20 seconds;

Parameter B: decrease in potential, as a percentage of parameter A, in the course of 20 seconds in the dark;

Parameter C: decrease in potential on exposure to actinic light, as a percentage of the initial potential directly before exposure;

Parameter D: change in potential, per second, at the beginning of exposure;

Parameter E: time in which the potential existing before exposure has decreased to half its value on exposure to actinic light; and Parameter F: potential difference between exposed and unexposed areas of the charged layers.

The results of the measurements are summarized in Table Ib.

TABLE Ib

| | Parameter | | | | | |
|---|---|---|---|---|---|---|
| Example | A [V] | B [%] | C [%] | D [V/s] | E [ms] | F [V] |
| I.1 | 1,100 | 41 | 99 | 5,300 | 175 | 640 |
| I.2 | 1,000 | 35 | 99 | 5,550 | 175 | 640 |
| I.3 | 1,250 | 38 | 99 | 3,600 | 220 | 765 |
| I.4 | 1,580 | 39 | 99 | 4,600 | 200 | 950 |
| Comparative Example | 400 | 48 | 83 | 3,450 | 305 | 210 |

Table Ib shows that layers containing the novel phenylhydrazones I exhibit less discharge in the dark, more rapid and more complete discharge on exposure to actinic light and, principally, substantially greater differentiation between exposed and unexposed areas. As a result of the last-mentioned property, substantially better toning of the recording materials subjected to imagewise exposure is achieved.

We claim:
1. A phenylhydrazone of the formula

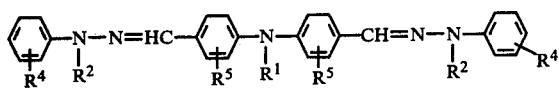

where $R^1$ is $C_1$-$C_4$-alkyl or phenyl-$C_1$-$C_4$-alkyl, or is phenyl which is unsubstituted or substituted by $C_1$-$C_4$-alkyl, $C_1$-$C_4$-alkoxy or halogen, or is a radical of the formula

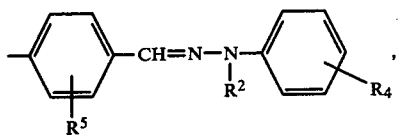

$R^2$ is $C_1$-$C_4$-alkyl or is phenyl which is unsubstituted or substituted by $C_1$-$C_4$-alkyl, $C_1$-$C_4$-alkoxy or halogen, and $R^4$ and $R^5$ independently of one another are each hydrogen, $C_1$-$C_4$-alkyl, $C_1$-$C_4$-alkoxy or halogen.

2. A phenylhydrazone as claimed in claim 1, wherein $R^1$ is methyl, ethyl or phenyl.

3. A phenylhydrazone as claimed in claim 1, wherein $R^2$ is methyl, ethyl or phenyl.

4. A phenylhydrazone as claimed in claim 1, wherein $R^1$ and $R^2$ independently of one another are each methyl, ethyl or phenyl.

5. A phenylhydrazone as claimed in claim 1, wherein $R^4$ and $R^5$ are each hydrogen.

6. A phenylhydrazone as claimed in claim 2, wherein $R^4$ and $R^5$ are each hydrogen.

7. A phenylhydrazone as claimed in claim 3, wherein $R^4$ and $R^5$ are each hydrogen.

8. A phenylhydrazone as claimed in claim 4, wherein $R^4$ and $R^5$ are each hydrogen.

9. A phenylhydrazone of the formula

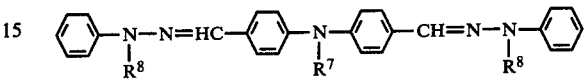

where $R^7$ and $R^8$ independently of one another are each methyl or phenyl.

10. A phenylhydrazone as claimed in claim 9, wherein $R^7$ and $R^8$ are each methyl.

11. A phenylhydrazone as claimed in claim 9, wherein $R^7$ and $R^8$ are each phenyl.

12. A phenylhydrazone as claimed in claim 9, wherein $R^7$ is phenyl and $R^8$ is methyl.

13. A phenylhydrazone as claimed in claim 9, wherein $R^7$ is methyl and $R^8$ is phenyl.

* * * * *